United States Patent

Randolph et al.

[11] Patent Number: 5,284,056
[45] Date of Patent: Feb. 8, 1994

[54] HYDROMETER FOR DETERMINING COOLANT FLUID ANTIFREEZE CONCENTRATION

[76] Inventors: Delbert D. Randolph, 2717 Augusta Ln. Apt. D, Hays, Kans. 67601; Gerald E. Wagnon, R.R. #1, Box 147, Great Bend, Kans. 67530

[21] Appl. No.: 59,512

[22] Filed: May 7, 1993

Related U.S. Application Data

[63] Continuation of Ser. No. 782,521, Oct. 24, 1991, abandoned.

[51] Int. Cl.⁵ ............................................. G01N 9/10
[52] U.S. Cl. ................................. 73/440; 73/863.41
[58] Field of Search ................ 73/440, 863.41, 444, 73/445, 446

[56] References Cited

U.S. PATENT DOCUMENTS

| | | | |
|---|---|---|---|
| 2,320,544 | 6/1943 | Gaus et al. | 73/863.61 |
| 3,188,565 | 6/1965 | Kolb | 73/863.41 |
| 3,626,763 | 12/1971 | White | 73/440 |
| 3,631,727 | 1/1972 | White | 73/440 |
| 4,649,747 | 3/1987 | Barber et al. | 73/440 |
| 4,702,109 | 10/1987 | Viola | 73/440 |
| 4,736,628 | 4/1988 | Lin | 73/440 |

*Primary Examiner*—Robert R. Raevis
*Assistant Examiner*—Michael Brock
*Attorney, Agent, or Firm*—John R. Flanagan

[57] ABSTRACT

A hydrometer for determining coolant fluid antifreeze concentration includes a housing having a pair of spaced openings for inflow and outflow of coolant fluid into and from the housing, a transparent view dome mounted in flow communication with the housing, a pair of identical sets of float balls of different specific gravities, a pair of longitudinal channels defined along opposite portions of the view dome in flow communication with the interior thereof and containing the sets of float balls for longitudinal movement relative to the view dome and for visual observation from the exterior of the view dome, and a dam defined in the housing between and spaced from the flow openings thereof and capable of obstructing the path of coolant fluid flow directly between the openings of the housing so as to cause deflection of coolant fluid flow into the transparent view dome and the channels therein.

19 Claims, 2 Drawing Sheets

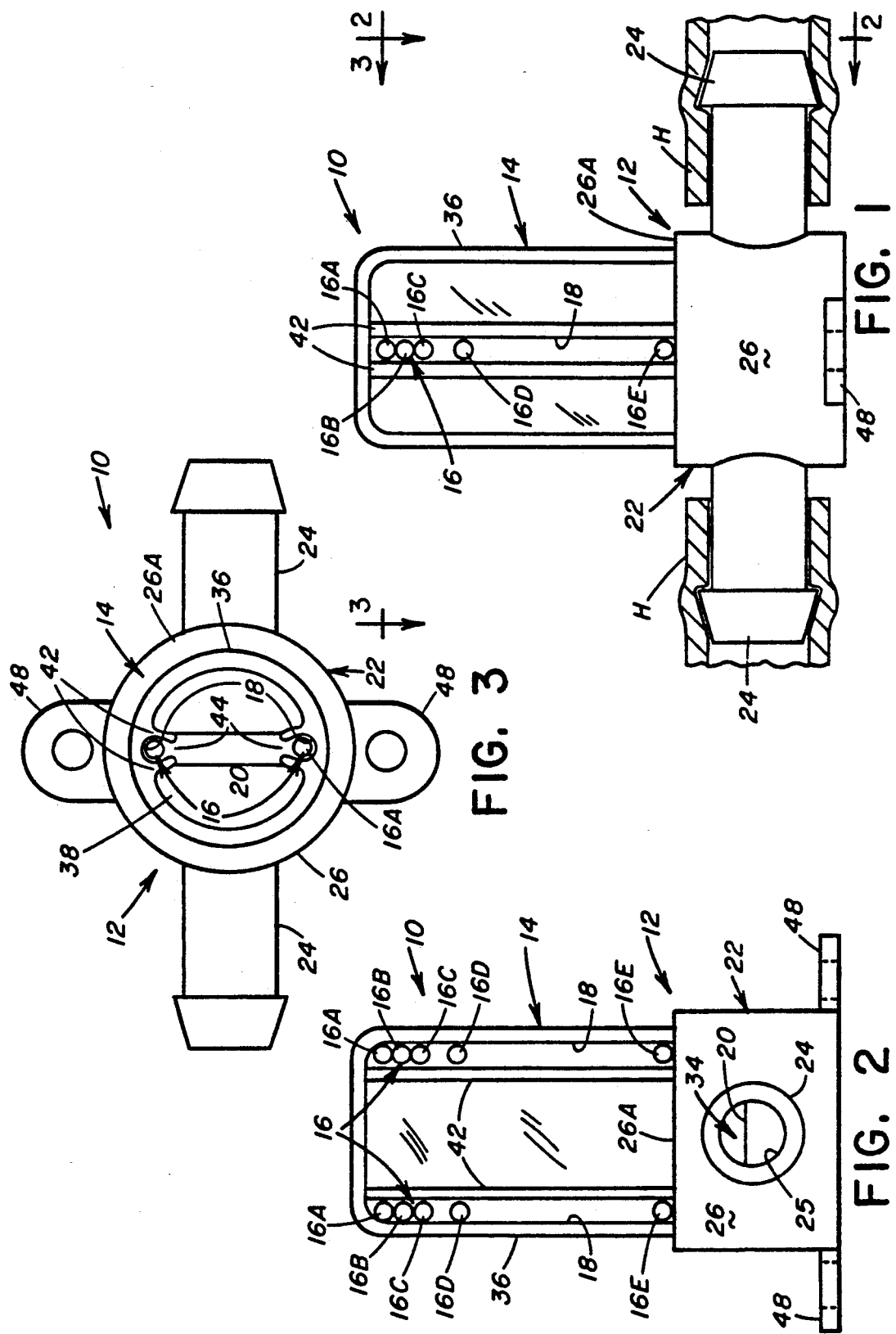

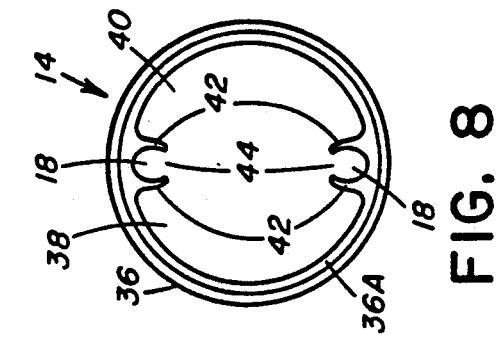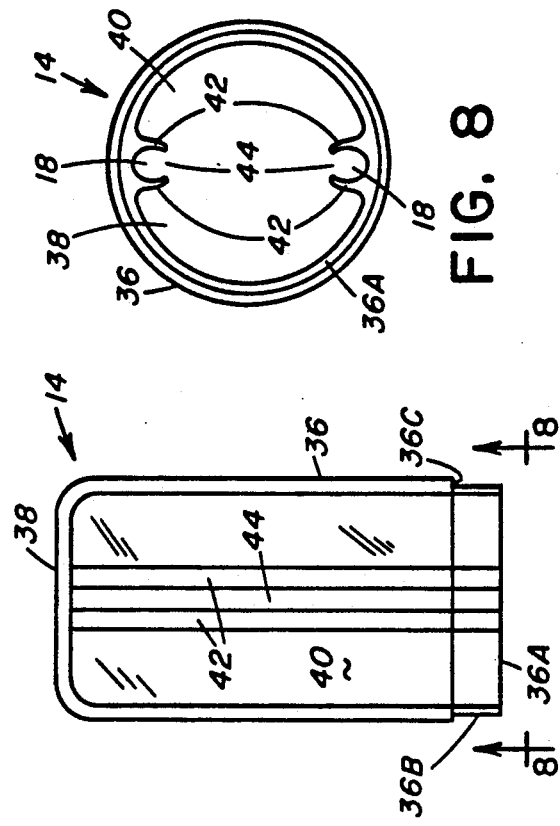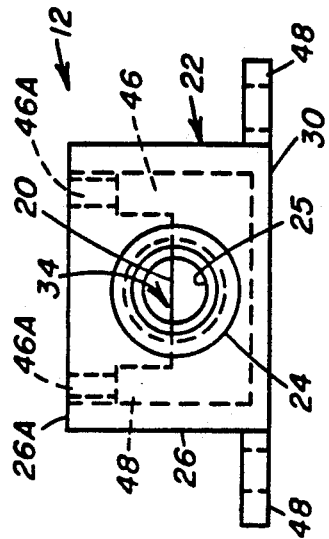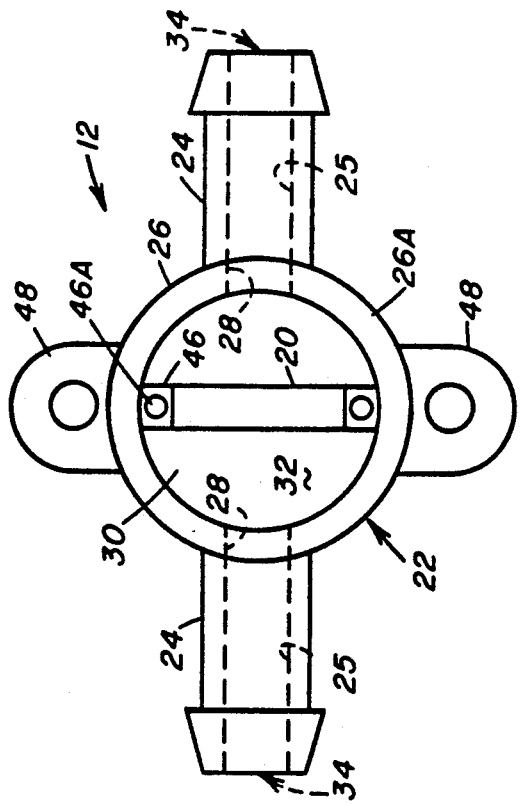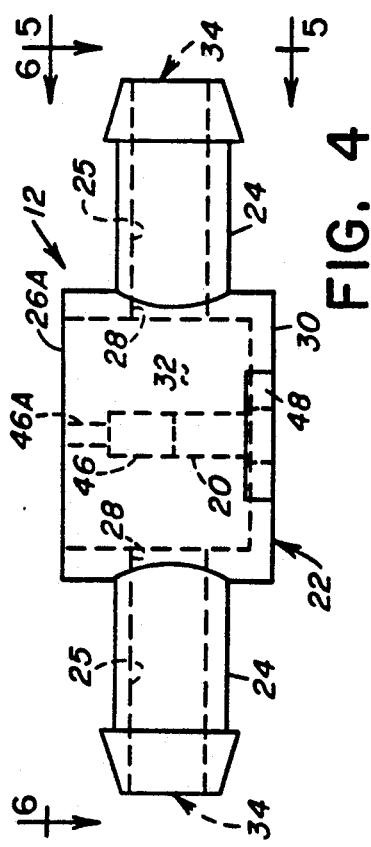

HYDROMETER FOR DETERMINING COOLANT FLUID ANTIFREEZE CONCENTRATION

This application is a continuation of application Ser. No. 07/782,521, filed Oct. 24, 1991, now abandoned.

BACKGROUND OF THE INVENTION

1. Field of the Invention

The present invention generally relates to hydrometers and, more particularly, is concerned with a hydrometer for testing engine coolant fluid and indicating visually the concentration, or level, of antifreeze in the coolant fluid.

2. Description of the Prior Art

Hydrometers have been used for many years to test the freezing points of coolant fluids in motor vehicles. Traditionally, these hydrometers have utilized float tubes with appropriate internal scales that provide a reading of the freezing point based upon the specific gravity of the coolant fluid. Such hydrometers provide an accurate reading, but are relatively delicate and costly to construct and maintain.

Ball-type hydrometers have been developed for medical applications which use balls of different specific gravity to continuously measure the specific gravity of the fluid. When a ball of a known specific gravity floats at the surface of the fluid, it is known that the specific gravity of the fluid is greater than that of the ball. By identifying which balls float on the surface of the fluid, the specific gravity of the fluid can be identified within a given range. Examples of these ball-type hydrometers are disclosed in U.S. Pat. Nos. 3,626,763 and 3,631,727 to White.

Several recent ball-type hydrometers suited for use in automotive applications are disclosed in U.S. Pat. No. 4,649,747 to Barber et al, U.S. Pat. No. 4,702,109 to Viola, and U.S. Pat. No. 4,736,628 to Lin. The ball-type hydrometers of the Viola and Lin patents have similar constructions. These hydrometers include a generally rectangular housing defining a row of vertical cavities partially partitioned from one another so as to contain a plurality of balls of different specific gravities while maintaining fluid communication with adjacent cavities. The housing and the partitioned cavities therein are open at the top and disposed in fluid communication with inlet and outlet tubes rigidly connected at opposite ends of the housing. The tubes are adapted for connection to fluid lines in an automotive coolant system.

The Barber et al patent discloses several versions of a hydrometer for connection in an engine coolant flow line. One version has a T-shaped fitting, a generally cylindrical transparent view dome, a cap for attaching the dome to the fitting, and a plurality of float balls of different specific gravity contained in a chamber defined by the dome. The fitting is composed of a main branch and a center branch. The main branch defines a straight flow passage and opposite inlet and outlet ends adapted to be directly connected in the coolant flow line. The center lateral branch is located intermediately between the inlet and outlet ends of the main branch. The center branch defines a flow passage extending transversely to the straight flow passage of the main branch. The transparent view dome is attached by the cap to the center lateral branch of the fitting and is located above the fitting when the fitting is properly oriented in its installed position. Also, an air release valve is installed on the top wall of the view dome for use in releasing air which might be trapped in the top of the dome. Alternatively, a venturi vent tube is installed axially in the view dome for establishing communication between the top of the dome and the flow passage of the main branch to evacuate air from the top of the dome.

A drawback of this one version of the Barber et al hydrometer is that it requires periodic servicing to ensure that it is working properly. The float balls used in the Barber et al hydrometer to visually indicate the strength of the antifreeze in the coolant fluid are loosely contained within the chamber defined by the view dome. Thus, a circular screen has to be employed at the bottom of the dome to prevent the balls from settling downward through the flow passage of the center branch into the flow passage of the main branch where they would escape into the engine coolant line. It is the presence of the screen that necessitates performance of periodic maintenance be performed on the hydrometer to clean the screen. To check and clean the screen, the cap and dome of the hydrometer must first be removed and then replaced.

The drawback of requiring periodic maintenance is that oftentimes it will be overlooked and thus not be done by the vehicle owner. As a result, the hydrometer may fail to perform its intended function of providing an accurate indication of the antifreeze strength.

Consequently, a need still remains for improvement of hydrometer design in order to make it as maintenance-free and as accurate as possible.

SUMMARY OF THE INVENTION

The present invention provides a hydrometer designed to satisfy the aforementioned needs. The hydrometer is particularly adapted for use in continuously testing coolant fluid and indicating the concentration, or level, of antifreeze in the coolant fluid. The hydrometer is designed to allow a continuous flow of coolant fluid through it which maintains its accuracy and provides substantially maintenance-free operation.

Accordingly, the present invention is directed to a hydrometer for determining coolant fluid antifreeze concentration. The hydrometer comprises: (a) a hollow housing having a pair of spaced flow openings for inflow and outflow of coolant fluid into and from the housing; (b) a transparent hollow view dome having an interior and an exterior and being mounted with its interior in flow communication with the housing; (c) a plurality of float elements of different specific gravities and having different identification markings thereon; (d) means defining at least one longitudinal channel along a portion of the view dome at the interior thereof and in flow communication with the interior thereof, the channel containing the float elements for longitudinal movement relative to the transparent view dome and for visual observation from the exterior thereof; and (e) means defining a dam in the housing between and spaced from the flow openings of the housing and capable of obstructing the path of coolant fluid flow directly between the flow openings so as to cause deflection of coolant fluid flow upwardly into the transparent view dome and the longitudinal channel.

More particularly, the housing including a hollow base and a pair of hollow connector members connected to and extending from the hollow base. The hollow base has a continuous sidewall open at its upper edge with a pair of spaced apertures defined in the sidewall, and a bottom wall connected to the bottom of the sidewall. The sidewall and bottom wall of the base together define a cavity therein. The hollow connector members are adapted for attaching to coolant fluid-carrying hoses and are connected to the sidewall of the base at the locations of the spaced apertures and together therewith defined the flow openings of the housing. The dam is a wall extending across the cavity of the hollow base and connected to the bottom wall and opposite portions of the sidewall of the base. The dam has a height that is less than the height of the sidewall of the base.

Also, the transparent view dome has a continuous sidewall and a top wall connected to the top of the sidewall. The sidewall of the view dome is open at a lower edge and connected to the upper edge of the sidewall of the housing base so as to extend above the housing base. The sidewall and top wall of the view dome together define a chamber in flow communication with the cavity of the base of the housing for receiving coolant fluid therefrom.

The longitudinal channel on the interior of the view dome extends from the lower edge of the sidewall to the top of the view dome and has a narrow opening slot defined along the longitudinal extent of the channel providing flow communication with the chamber of the view dome. The float elements are disposed in the longitudinal channel in a predetermined arrangement such that the specific gravities of individual float elements decreases incrementally from a lowermost one to an uppermost one of the float elements in the channel.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 1 is a side elevational view of a hydrometer of the present invention.

FIG. 2 is an end elevational view of the hydrometer as seen along line 2—2 of FIG. 1.

FIG. 3 is a top plan view of the hydrometer as seen along line 3—3 of FIG. 1.

FIG. 4 is a side elevational view of a housing of the hydrometer of FIG. 1.

FIG. 5 is an end elevation view of the hydrometer housing as seen along line 5—5 of FIG. 4.

FIG. 6 is a top plan view of the hydrometer housing as seen along line 6—6 of FIG. 4.

FIG. 7 is a side elevational view of a transparent view dome of the hydrometer of FIG. 1.

FIG. 8 is a bottom plan view of the hydrometer view dome as seen along line 8—8 of FIG. 7.

DETAILED DESCRIPTION OF THE INVENTION

Referring to FIGS. 1-3 of the drawings, there is illustrated a hydrometer of the present invention, being generally designated 10. The hydrometer 10 is adapted for permanent installation in an engine (or non-engine) coolant system by attachment with ends of the hoses H of the coolant system. When so installed, the hydrometer 10 is capable, on a continuous basis, of testing the engine coolant fluid and indicating visually the antifreeze level, or concentration, in the coolant fluid. In its basic components, the hydrometer 10 includes a hollow housing 12, a transparent hollow view globe or dome 14, at least one and preferably two sets of float elements in the form of balls 16 of different specific gravities, at least one and preferably two channels 18 defined in the interior of the view dome 14 for containing the sets of float balls 16, and a dam 20 disposed in the housing 12.

Referring to FIGS. 1-6, the housing 12 of the hydrometer 10 includes a hollow base 22 and a pair of hollow tubular connector members 24 attached to and extending from opposite sides of the base 22. The hollow connector members 24 have central passages 25 extending between their opposite ends and exterior profiles configured to adapt them for insertion into and clamping with ends of coolant fluid-carrying hoses H.

The hollow base 22 of the hydrometer housing 12 includes a continuous cylindrical sidewall 26 open at an upper peripheral edge 26A, with a pair of spaced circular apertures 28 defined in opposite portions of the sidewall 26. The base 22 also includes a bottom wall 30 connected to a bottom of the sidewall 26. The bottom wall 30 and sidewall 26 of the hollow base 22 together define a cavity 32 therein. The hollow connector members 24 are connected to the sidewall 26 of the hollow base 22 at the locations of the spaced apertures 28. The central passages 25 through the hollow connectors 24 together with the apertures 28 in the sidewall 26 define a pair of spaced flow openings 34 of the housing 12 for permitting inflow and outflow of coolant fluid to and from the housing 12. Preferably, the hollow base 22 and hollow connector members 24 of the housing 12 are fabricated as separate pieces by injection molding a suitable plastic material. Then the base 22 and connector members 24 are attached together by use of any suitable method which will bond them together permanently.

Referring to FIGS. 1-3, 7 and 8, the hollow view dome 14 is fabricated from a suitable transparent plastic material. The view dome 14 includes a continuous cylindrical sidewall 36, being open at a lower peripheral edge 36A, and a top wall 38 connected to a top of the sidewall 36. At the exterior of the view dome 14, the lower peripheral edge 36A of the sidewall 36 has an annular recess 36B defining a downwardly-facing annular shoulder 36C. The lower peripheral edge 36A of the sidewall 36 of the view dome 14 fits within the upper peripheral edge 26A of the sidewall 26 of the housing base 22 to where the shoulder 36C on the view dome sidewall 36 seats on the upper peripheral edge 26A of the base sidewall 26. The view dome 14 and housing base 22 are sealed together by use of any suitable method which will bond them together permanently. The view dome 14 extends above the housing 12 and the sidewall 36 and top wall 38 of the view dome 14 together define a chamber 40 in flow communication with the cavity 32 of the housing base 22 for receiving coolant fluid therefrom.

Referring still to FIGS. 1-3, 7 and 8, the transparent view dome 14 includes two pairs of spaced longitudinal rails 42 formed longitudinally along opposite portions of the view dome sidewalls 36 on the interior thereof. Each pair of spaced rails 42 defines one of the longitudinal channels 18. The rails 42 of each pair thereof have arcuate cross-sectional shapes which provide the channel 18 with a generally circular cross-sectional shape. The pairs of longitudinal rails 42 extend from the lower peripheral edge 36A of the sidewall 36 to the top wall 38 of the view dome 14. Each pair of spaced rails 42 define a narrow open slot 44 along the extent of the longitudinal channel 18 for establishing flow communication with the chamber 40 of the view dome 14.

Each longitudinal channel 18 contains one set of the float balls 16 and, as seen in FIG. 2, is slightly larger in diameter than each float ball 16 so as to provide freedom of longitudinal movement of the float balls 16 only vertically along the channels 18 relative to the transparent view dome 14, restricting the float balls 16 from moving randomly about the chamber 40 of the view dome 14. The transparency of the view dome 14 and the locations of the channels 18 contiguously along the opposite sidewall portions of the view dome 14 allow for clear visual observation of the balls 16 from the exterior of the view dome 14.

The float balls 16 of the identical sets thereof have different specific gravities and different identification markings thereon. The float balls 16 of one set are disposed in the respective longitudinal channel 18 in a predetermined arrangement such that the specific gravities of individual float balls 16 decreases incrementally from a lowermost one to an uppermost one of said float balls 16 in the channel 18. Preferably, the identification markings of the float balls 16 are different colors. As seen in FIGS. 1 and 2, the float balls 16A, 16B, 16C which are formulated to float at incrementally lesser specific gravities of the coolant fluid will float higher in the channels 18 of the view dome 14 than the float balls 16D, 16E which are formulated to float at incrementally greater specific gravities of the coolant fluid.

For example, if the uppermost float ball 16A in each channel 18, being green in color, rises to the top of the channel 18, then this can mean that the coolant fluid will resist freezing down to +20° F. If the next uppermost float ball 16B in each channel 18, being red in color, rises to the top of the channel 18, then this can mean that the coolant fluid will resist freezing down to +5° F. If the third or middle float ball 16C in each channel 18, being yellow in color, rises to the top of the channel 18, then this can mean that the coolant fluid will resist freezing down to −10° F. If the next lowermost float ball 16D in each channel 18, being white in color, rises to the top of the channel 18, then this can mean that the coolant fluid will resist freezing down to −25° F. Finally, if the lowermost float ball 16E in each channel 18, being blue in color, rises to the top of the channel 18, then this can mean that the coolant fluid will resist freezing down to −40° F. It should be understood that the present invention is not restricted to the use of any particular number of float balls 16 nor to the use of colored balls. Float balls 16 of a single color can be utilized, if desired, in which case the number of balls rising to the top of the channels 18 would indicate the strength of the antifreeze since the increments represented by each ball, such as 15° F., would be known. In any event, in such manner the float balls 16 provide a direct visual indication of the strength of the antifreeze in the coolant fluid.

Referring to FIGS. 1 and 4–6, the dam 20 is in the form of a wall 20 disposed in the housing base 22 between and spaced from the opposite apertures 28 in the base sidewall 26. The dam wall 20 extends across the cavity 32 of hollow base 22 and is connected to the bottom wall 30 and opposite portions of the sidewall 26 of the housing base 22. The dam wall 20 has a height approximately equal to one-half the height of the base sidewall 26 and thus blocks approximately the lower half of a direct flow path between the sidewall apertures 28. Therefore, the dam wall 20 is capable of obstructing the path of coolant fluid flow directly between the flow openings 34 so as to cause deflection of coolant fluid flow temporarily from the housing base 22 into the transparent view dome 14 and the longitudinal channels 18 and into contact with the float balls 16.

It should be mentioned that the hydrometer 10 of the present invention functions best when a pocket of air is present above the top surface of the coolant fluid in the view dome 14 below the top wall 38 thereof. Thus, no means of venting this air pocket is necessary nor should be provided. Also, the hydrometer 10 functions best when the coolant fluid in the view dome 14 is in a state of turbulence. The presence of the dam wall 20 ensures that a turbulent fluid state will exist in the view dome 14.

Also, at opposite ends of the dam wall 20, a pair of pedestals 46 extend upright from the dam wall 20. The pedestals 46 have cylindrical upper portions 46A which fit into and close the lower ends of the channels 18 when the view dome 14 is seated on the housing base 22. Also, a pair of opposing flanges 48 are provided on the exterior of the housing base bottom wall 30 for mounting the hydrometer 10 in a stationary position.

It is thought that the present invention and its advantages will be understood from the foregoing description and it will be apparent that various changes may be made thereto without departing from its spirit and scope of the invention or sacrificing all of its material advantages, the form hereinbefore described being merely preferred or exemplary embodiment thereof.

What is claimed is:

1. A hydrometer for determining coolant fluid antifreeze concentration, comprising:
   (a) a hollow housing having a pair of spaced openings for inflow and outflow of coolant fluid to and from said housing;
   (b) a transparent hollow view dome having an interior and an exterior and being mounted upon and extending above said housing with said interior in flow communication with said housing;
   (c) a plurality of float elements of different specific gravities;
   (d) a pair of spaced longitudinal rails disposed above said housing and connected to and extending vertically along a portion of a sidewall of said transparent view dome on said interior of said view dome to define a longitudinal channel, said spaced longitudinal rails defining a narrow slot therebetween along the extent of said channel for establishing flow communication with said interior of said view dome, said longitudinal rails having predetermined cross-sectional shapes providing said longitudinal channel with a predetermined cross-sectional shape for movably containing said float elements and for restricting said float elements to only substantially vertical longitudinal movement relative to said transparent view dome and for visual observation from said exterior thereof; and
   (e) means for defining a dam in the housing between and spaced from said openings of said housing and below said view dome and being capable of obstructing the path of coolant fluid flow directly between said openings so as to cause deflection of coolant fluid flow into and from said transparent view dome and said longitudinal channel.

2. The hydrometer of claim 1 wherein said view dome includes:

a continuous sidewall connected at a lower edge to said housing so as to extend above said housing; and a top wall connected to a top of said sidewall, said top wall and sidewall of said view dome together defining a chamber in flow communication with said housing for receiving coolant fluid therefrom.

3. The hydrometer of claim 2 wherein said pair of spaced longitudinal rails extend from said lower edge of said sidewall to said top wall of said view dome.

4. The hydrometer of claim 3 wherein said float elements are disposed in said longitudinal channel in a predetermined arrangement such that the specific gravities of individual float elements decreases incrementally from a lowermost one to an uppermost one of said float elements in said channel.

5. The hydrometer of claim 1 wherein said housing includes:

a hollow base having a pair of spaced apertures and defining a cavity in flow communication with said apertures and said interior of said transparent view dome; and a pair of hollow connector members connected to and extending from said hollow base and being adapted for attaching to coolant fluid-carrying hoses, said hollow connectors being connected to said hollow base at the locations of said spaced apertures and together therewith defining said flow openings of said housing.

6. The hydrometer of claim 5 wherein said view dome includes:

a continuous sidewall connected at a lower edge to said housing base so as to extend above said housing base; and a top wall connected to a top of said sidewall, said top wall and sidewall together defining a chamber in flow communication with said cavity of said base of said housing for receiving coolant fluid therefrom.

7. The hydrometer of claim 5 wherein said hollow base includes:

a continuous sidewall open at an upper edge with said spaced apertures defined in said sidewall; and a bottom wall connected to a bottom of said sidewall, said bottom wall and sidewall of said base together defining said cavity therein.

8. The hydrometer of claim 7 wherein said view dome includes:

a continuous sidewall being open at a lower edge and connected to said upper edge of said sidewall of said housing base so as to extend above said housing base; and a top wall connected to a top of said sidewall, said top wall and sidewall together defining a chamber in flow communication with said cavity of said base of said housing for receiving coolant fluid therefrom.

9. The hydrometer of claim 7 wherein said dam is a wall extending across said cavity of said hollow base and connected to said bottom wall and opposite portions of said sidewall thereof, said dam having a height that is less than the height of said sidewall of said base.

10. A hydrometer for determining coolant fluid antifreeze concentration, comprising:

(a) a hollow housing having a pair of spaced openings for inflow and outflow of coolant fluid to and from said housing;

(b) a transparent hollow view dome having an interior and an exterior and being mounted upon and extending above said housing with said interior in flow communication with said housing;

(c) a pair of identical sets of float balls of different specific gravities;

(d) first and second pairs of spaced longitudinal rails disposed above said housing and connected to and extending vertically along opposite portions of a sidewall of said transparent view dome to define respective longitudinal channels, each of said pairs of spaced longitudinal rails defining a narrow slot therebetween along the extent of said respective channel for establishing flow communication with said interior of said view dome, said longitudinal rails of each pair thereof having predetermined cross-sectional shapes providing each of said longitudinal channels with a predetermined cross-sectional shape for movably containing one of said pair of sets of said float balls and for restricting said float balls to only substantially vertical longitudinal movement relative to said transparent view dome and for visual observation from said exterior thereof; and (e) means for defining a dam in the housing between and spaced from said openings of said housing and below said view dome and being capable of obstructing the path of coolant fluid flow directly between said openings so as to cause deflection of coolant fluid flow into and from said transparent view dome and said longitudinal channels.

11. The hydrometer of claim 10 wherein said housing includes:

a hollow base having a pair of spaced apertures and defining a cavity in flow communication with said apertures and said interior of said transparent view dome; and a pair of hollow connector members connected to and extending from said hollow base and being adapted for attaching to coolant fluid-carrying hoses, said hollow connectors being connected to said hollow base at the locations of said spaced apertures and together therewith defining said flow openings of said housing.

12. The hydrometer of claim 11 wherein said view dome includes:

a continuous sidewall connected at a lower edge to said housing base so as to extend above said housing base; and a top wall connected to a top of said sidewall, said top wall and sidewall together defining a chamber in flow communication with said cavity of said base of said housing for receiving coolant fluid therefrom.

13. The hydrometer of claim 12 wherein each of said pair of spaced longitudinal rails extend from said lower edge of said sidewall to said top wall of said view dome.

14. The hydrometer of claim 13 wherein each of said sets of float balls is disposed in one of said longitudinal channels in a predetermined arrangement such that the specific gravities of individual float balls decreases incrementally from a lowermost one to an uppermost one of said float balls in said channel.

15. The hydrometer of claim 11 wherein said hollow base includes:

a continuous sidewall open at an upper edge with said spaced apertures defined in said sidewall; and a bottom wall connected to a bottom of said sidewall, said bottom wall and sidewall of said base together defining said cavity therein.

16. The hydrometer of claim 15 wherein said view dome includes:
   a continuous sidewall being open at a lower edge and connected to said upper edge of said sidewall of said housing base so as to extend above said housing base; and
   a top wall connected to a top of said sidewall, said top wall and sidewall together defining a chamber in flow communication with said cavity of said base of said housing for receiving coolant fluid therefrom.

17. The hydrometer of claim 15 wherein said dam is a wall extending across said cavity of said hollow base and connected to said bottom wall and opposite portions of said sidewall thereof, said dam having a height that is less than the height of said sidewall.

18. A hydrometer for determining coolant fluid antifreeze concentration, comprising:
   (a) a housing including a hollow base and a pair of hollow connector members connected to and extending from opposite sides of said base and each adapted for attaching to a coolant fluid-carrying hose, said hollow base having a continuous sidewall with a pair of spaced apertures defined therein and a bottom wall and connected to the bottom of said sidewall, said bottom wall and sidewall of said base together defining a cavity therein, said hollow connector members being connected to said sidewall of said hollow base at the locations of said apertures for defining a pair of spaced openings for inflow and outflow of coolant fluid to and from said housing;
   (b) a transparent view dome having an exterior and an interior and including a continuous sidewall and a top wall connected to a top of said sidewall, said view dome being open at a lower edge of said sidewall and connected to an upper edge of said sidewall of said hollow base so as to extend above said base, said sidewall and top wall of said view dome together defining a chamber in flow communication with said cavity of said hollow base for receiving coolant fluid therefrom;
   (c) a plurality of float balls of different specific gravities;
   (d) a pair of spaced longitudinal rails disposed above said housing and connected to and extending vertically along an interior portion of said sidewall of said view dome from said lower edge thereof to said top wall thereof to define a longitudinal channel, said spaced longitudinal rails defining a narrow slot therebetween along the extend of said channel for establishing flow communication with said chamber of said view dome, said longitudinal rails having predetermined cross-sectional shapes providing said longitudinal channel with a predetermined cross-sectional shape for movably containing float balls and for restricting said float balls to only substantially vertical longitudinal movement relative to said transparent view dome and for visual observation from said exterior thereof, said float balls being contained in said longitudinal channel in a predetermined arrangement such that the specific gravities of individual float balls decrease incrementally from a lowermost one to an uppermost one of said float balls in said channel; and
   (e) means connected to the interior of said hollow base for defining a dam in the housing between and spaced from said openings of said housing and below said view dome and being capable of obstructing the path of coolant fluid flow directly between said openings so as to cause deflection of coolant fluid flow into and from said transparent view dome and said longitudinal channel.

19. The hydrometer of claim 18 wherein said dam is a wall extending across said cavity of said hollow base and connected to said bottom wall and opposite portions of said sidewall thereof, said dam having a height that is less than the height of said sidewall.

* * * * *